(12) United States Patent
Dumas

(10) Patent No.: US 7,393,970 B2
(45) Date of Patent: Jul. 1, 2008

(54) BORON CARBIDE AS AN EFFECTIVE FRIEDEL-CRAFTS TYPE CATALYST

(75) Inventor: Philip Edward Dumas, Morrisville, PA (US)

(73) Assignee: The College of N.J, Ewing, NJ (US)

(\*) Notice: Subject to any disclaimer, the term of this patent is extended or adjusted under 35 U.S.C. 154(b) by 0 days.

(21) Appl. No.: 11/897,507

(22) Filed: Aug. 31, 2007

(65) Prior Publication Data

US 2008/0058545 A1 Mar. 6, 2008

Related U.S. Application Data

(62) Division of application No. 11/442,716, filed on May 30, 2006, now Pat. No. 7,279,604.

(51) Int. Cl.
*C07C 69/76* (2006.01)

(52) U.S. Cl. .................. 560/109; 560/106

(58) Field of Classification Search ............ 560/106, 560/109
See application file for complete search history.

(56) References Cited

U.S. PATENT DOCUMENTS

| 4,414,406 A | 11/1983 | Fielas |
| 4,547,605 A | 10/1985 | Kresge |
| 4,717,780 A | 1/1988 | Olson |
| 5,750,455 A | 5/1998 | Chauvin |
| 6,184,418 B1 | 2/2001 | Dubac |

OTHER PUBLICATIONS

Tamaddon et al□□A green protocol for chemoselective O-acylation in the presence of zinc oxide as a heterogeneous, reusable and eco-friendly catalyst □□Tetrahedron Letters □□vol. 46, Issue 45, Nov. 7, 2005, pp. 7841-7844 □□.*

\* cited by examiner

*Primary Examiner*—Jafar Parsa

(57) ABSTRACT

The compound boron carbide, $B_4C$, is an effective catalyst for the synthesis of aromatic esters by reacting benzoyl halides with phenols in the presence of powdered $B_4C$.

2 Claims, No Drawings

BORON CARBIDE AS AN EFFECTIVE FRIEDEL-CRAFTS TYPE CATALYST

CROSS REFERENCED TO RELATED APPLICATION

This application is a divisional of application Ser. No. 11/442,716 filed May 30, 2006 now U.S. Pat. No. 7,279,604 examined by J. Parsa.

BACKGROUND

Friedel-Craft alkylation and acylation reactions of organic compounds have been commonly performed with Lewis acid catalysts. However, the use of Lewis acid catalysts in commercial practice has presented problems of the catalysts being corrosive, difficult to recover, and the generation of hazardous waste.

Examples of such reactions are described in the text by P. Bruice, Organic Chemistry, $4^{th}$ edition, Prentice Hall, 2004, pg. 612 and following. A common catalyst employed in both alkylation and acylation reactions is the Lewis acid $AlCl_3$. Although $AlCl_3$ is referred to as a catalyst in the true sense, it is not. It requires stoichiometric amounts of $AlCl_3$ since it actually forms a complex with the reactant that subsequently requires its removal from the reaction mixture by either an acid or base hydrolysis. Such a procedure is costly and, in the process toxic waste is generated which must be disposed of. Other Lewis acid catalysts have been investigated which include zeolites as disclosed in U.S. Pat. Nos. 4,547,605 and 4,717,780. Although the zeolites are effective Lewis acid catalysts there use is often limited by the pore size of the zeolite which inhibit large sterically hindered molecules from reaching the active site within the zeolite.

Numerous Lewis acid catalysts have been disclosed which include both transition and non-transition metals as disclosed in U.S. Pat. No. 4,414,406 and U.S. Pat. No. 6,184,418, however often the catalysts are difficult to prepare or exhibit chemical reactivity that limits their use. Numerous disclosures include the utilization of mixed catalysts as described in U.S. Pat. No. 5,750,455.

Although much effort has been made to develop more effective catalysts for both alkylation and acylation of organic compounds there is a need for more effective catalysts that do not have the inherent problems of those currently employed. An ideal catalyst would be one that functions as a heterogenous catalyst, easily removed from the reactants and products, chemically and thermally stable, and readily available or easily prepared, and inexpensive.

SUMMARY OF THE INVENTION

I have discovered that boron carbide, $B_4C$ is an effective catalyst for Friedel-Crafts type reactions. It is readily available, chemically and thermally stable, requires no pretreatment, and is easily recoverable from the reactants and reaction products.

Since $B_4C$ functions as a heterogenous catalyst and is non-toxic, no hazardous waste is generated at the conclusion of the reaction. The use of $B_4C$ requires no time consuming work up at the end of the reaction and can be reused without any regeneration or activation procedures. This discovery is unexpected since $B_4C$ is regarded in the literature as compound that is essentially unreactive.

DETAILED DESCRIPTION OF THE INVENTION

The current literature teaches that catalysts for Friedel-Crafts reactions are classified as Lewis acid catalysts. Although many materials have been investigated as Friedel-Craft catalysts they are all recognized as Lewis acid type catalysts. These include zeolites, clays, heteropoly acids, and various metal halides.

I have discovered that the non-metal carbide, boron carbide, $B_4C$ can function as a catalyst in acylation of aromatic compounds, previously conducted by Lewis acid Friedel-Craft type catalysts. This is unexpected since boron carbide is regarded as a compound that has a high resistance to chemical attack.

Boron carbide in an extremely hard material whose melting point is 2450° C. It is commonly used as an abrasive in lapping applications and as a refractory. It is also known to be a neutron absorber and is use in the nuclear industry. There are no reports in the chemical literature that boron carbide exhibits any chemical or physical properties that would indicate that it would function as a catalyst. This unexpected discovery is surprising in regard to the teachings in the prior art.

Boron carbide catalyzed the reaction of acyl haldides and phenols to produce the corresponding esters. High yields of phenyl benzoate were obtained by reacting benzoyl chloride with phenol in the presence of the powdered boron carbide catalyst.

The following example illustrates the embodiments of this invention, however, it is understood, it is presented only for illustrative purposes and do not limit the scope of this invention.

EXAMPLE

A mixture of 6.3 gm (0.05 mole) of benzoyl chloride and 4.7 gm (0.05 moles) of phenol and 0.1 gm of boron carbide was heated to about 60° C. for 12 hours. The semi-solid material was allowed to cool to room temperature. A solid material was recovered and dissolved in acetone, then filtered to remove the boron carbide catalyst. The acetone was removed at reduced pressure and the remaining solid was identified as phenyl benzoate by its infrared spectra. The yield of product was 93%.

The invention claimed is:

1. A process to produce aromatic esters by reacting benzoyl chloride with phenol in the presence of the catalysts boron carbide at a temperature of 40° to 120° C.

2. The process in claim 1 in which the reactants are substituted benzoyl chlorides and alkyl substituted phenols.

\* \* \* \* \*